(12) United States Patent
Gross (10) Patent No.: US 11,123,197 B2
(45) Date of Patent: Sep. 21, 2021

(54) HYDROPNEUMATIC ARTIFICIAL INTERVERTEBRAL DISC

(71) Applicant: RAINBOW MEDICAL LTD., Herzeliyah (IL)

(72) Inventor: Yossi Gross, Moshav Mazor (IL)

(73) Assignee: RAINBOW MEDICAL LTD., Herzliya (IL)

(*) Notice: Subject to any disclaimer, the term of this patent is extended or adjusted under 35 U.S.C. 154(b) by 105 days.

(21) Appl. No.: 16/558,987

(22) Filed: Sep. 3, 2019

(65) Prior Publication Data

US 2021/0059830 A1  Mar. 4, 2021

(51) Int. Cl.
*A61F 2/44* (2006.01)
*A61F 2/48* (2006.01)
*A61F 2/30* (2006.01)

(52) U.S. Cl.
CPC ............ *A61F 2/441* (2013.01); *A61F 2/4425* (2013.01); *A61F 2002/30668* (2013.01); *A61F 2002/482* (2013.01); *A61F 2002/487* (2013.01)

(58) Field of Classification Search
CPC ............ A61F 2/44–447; A61F 2002/482–487
See application file for complete search history.

(56) References Cited

U.S. PATENT DOCUMENTS

| | | |
|---|---|---|
| 2,959,410 A | 11/1960 | Fullam et al. |
| 4,044,774 A | 8/1977 | Corbin et al. |
| 4,503,863 A | 3/1985 | Katims |
| 5,088,977 A | 2/1992 | Sibalis |

(Continued)

FOREIGN PATENT DOCUMENTS

| | | |
|---|---|---|
| WO | 94/05369 | 3/1994 |
| WO | 01/52931 | 7/2001 |

(Continued)

OTHER PUBLICATIONS

Karran Sep. E et201 al., 1 "The Amyloid cascade hypothesis for AD," Nature Reviews Drug Discovery, vol. 10; 698-712.

(Continued)

*Primary Examiner* — Eduardo C Robert
*Assistant Examiner* — Steven J Cotroneo
(74) *Attorney, Agent, or Firm* — Sughrue Mion, PLLC (57) ABSTRACT

An artificial intervertebral disc (IVD) is provided for replacement of a degenerated intervertebral disc. The artificial IVD includes two endplates having oppositely-facing outward surfaces configured to engage respective intervertebral surfaces of the spinal column, and a chamber, which is disposed between oppositely-facing inner surfaces of the two endplates, and which includes a lateral wall including an electroosmotic membrane. A plurality of exposed electrode surface includes (i) one or more intra-chamber exposed electrode surfaces, which are located within the chamber; and (ii) one or more extra-chamber exposed electrode surfaces, which are located outside the chamber, in a vicinity of the chamber. Control circuitry is configured to drive at least one of the one or more intra-chamber exposed electrode surfaces and at least one of the one or more extra-chamber exposed electrode surfaces to electroosmotically drive liquid from outside the chamber to inside the chamber. Other embodiments are also described.

28 Claims, 7 Drawing Sheets

(56) References Cited

U.S. PATENT DOCUMENTS

| | | |
|---|---|---|
| 5,121,754 A | 6/1992 | Mullett |
| 5,433,739 A | 7/1995 | Sluijter et al. |
| 5,529,574 A | 6/1996 | Frackelton |
| 5,587,297 A | 12/1996 | Jacobson et al. |
| 5,792,100 A | 8/1998 | Shantha |
| 5,911,223 A | 6/1999 | Weaver et al. |
| 5,919,163 A | 7/1999 | Glickman |
| 5,938,690 A | 8/1999 | Law et al. |
| 6,041,252 A | 3/2000 | Walker et al. |
| 6,146,380 A | 11/2000 | Racz et al. |
| 6,161,047 A | 12/2000 | King et al. |
| 6,360,750 B1 | 3/2002 | Gerber et al. |
| 6,506,408 B1 | 1/2003 | Palasis |
| 6,567,702 B1 | 5/2003 | Nekhendzy et al. |
| 6,591,138 B1 | 7/2003 | Fischell et al. |
| 6,602,248 B1 | 8/2003 | Sharps et al. |
| 6,620,155 B2 | 9/2003 | Underwood et al. |
| 6,907,295 B2 | 6/2005 | Gross et al. |
| 6,941,172 B2 | 9/2005 | Nachum |
| 6,997,941 B2 | 2/2006 | Sharkey et al. |
| 7,120,489 B2 | 10/2006 | Shalev et al. |
| 7,217,351 B2 | 5/2007 | Krumme |
| 7,223,227 B2 | 5/2007 | Pflueger |
| 7,270,659 B2 | 9/2007 | Ricart et al. |
| 7,398,121 B2 | 7/2008 | Matsumura et al. |
| 7,509,171 B2 | 3/2009 | DiMauro |
| 7,640,062 B2 | 12/2009 | Shalev |
| 7,831,306 B2 | 11/2010 | Finch et al. |
| 7,860,569 B2 | 12/2010 | Solberg et al. |
| 8,190,248 B2 | 5/2012 | Besio et al. |
| 8,457,761 B2 | 6/2013 | Wariar |
| 8,577,469 B2 * | 11/2013 | Gross ............... A61N 1/326 607/43 |
| 8,676,348 B2 | 3/2014 | Gross |
| 9,616,221 B2 | 4/2017 | Gross |
| 9,724,513 B2 | 8/2017 | Lane et al. |
| 9,770,591 B2 | 9/2017 | Gross et al. |
| 9,950,156 B2 | 4/2018 | Gross et al. |
| 10,765,527 B2 * | 9/2020 | Chin ............... A61F 2/442 |
| 2002/0151948 A1 | 10/2002 | King et al. |
| 2002/0183683 A1 | 12/2002 | Lerner |
| 2003/0130707 A1 | 7/2003 | Gan et al. |
| 2003/0158589 A1 | 8/2003 | Katsnelson |
| 2003/0216792 A1 | 11/2003 | Levin et al. |
| 2003/0225331 A1 * | 12/2003 | Diederich ............... A61B 18/04 600/437 |
| 2004/0002746 A1 | 1/2004 | Ryan et al. |
| 2004/0019381 A1 | 1/2004 | Pflueger |
| 2004/0049180 A1 | 3/2004 | Sharps et al. |
| 2004/0083002 A1 * | 4/2004 | Belef ............... A61F 2/441 623/17.16 |
| 2004/0116977 A1 | 6/2004 | Finch et al. |
| 2004/0186576 A1 * | 9/2004 | Biscup ............... A61F 2/442 623/17.12 |
| 2004/0210209 A1 | 10/2004 | Yeung et al. |
| 2004/0225363 A1 | 11/2004 | Richelsoph |
| 2004/0253304 A1 | 12/2004 | Gross et al. |
| 2004/0267240 A1 | 12/2004 | Gross et al. |
| 2005/0010205 A1 | 1/2005 | Hovda et al. |
| 2005/0021104 A1 | 1/2005 | DiLorenzo |
| 2005/0058701 A1 | 3/2005 | Gross et al. |
| 2005/0119650 A1 | 6/2005 | Sanders et al. |
| 2005/0159790 A1 | 7/2005 | Shalev |
| 2005/0277996 A1 | 12/2005 | Podhajsky et al. |
| 2006/0030895 A1 | 2/2006 | Simon et al. |
| 2006/0106430 A1 | 5/2006 | Fowler et al. |
| 2006/0224223 A1 | 10/2006 | Podhajsky et al. |
| 2006/0276844 A1 | 12/2006 | Alon et al. |
| 2006/0293723 A1 | 12/2006 | Whitehurst et al. |
| 2007/0000784 A1 * | 1/2007 | Paul ............... G05D 7/0694 204/600 |
| 2007/0073402 A1 * | 3/2007 | Vresilovic ............... A61L 27/52 623/17.12 |
| 2007/0213700 A1 | 9/2007 | Davison et al. |
| 2007/0276201 A1 * | 11/2007 | Lee ............... A61B 5/4566 600/301 |
| 2008/0009927 A1 | 1/2008 | Vilims |
| 2008/0063703 A1 | 3/2008 | Gross et al. |
| 2008/0119907 A1 | 5/2008 | Stahmann |
| 2008/0177392 A1 * | 7/2008 | Williams ............... A61F 2/4611 623/17.16 |
| 2008/0188837 A1 | 8/2008 | Belsky et al. |
| 2008/0260542 A1 | 10/2008 | Nishikawa et al. |
| 2008/0275430 A1 | 11/2008 | Belsky et al. |
| 2009/0112278 A1 | 4/2009 | Wingeier et al. |
| 2009/0125080 A1 | 5/2009 | Montgomery |
| 2009/0126813 A1 | 5/2009 | Yanagisawa et al. |
| 2009/0131850 A1 | 5/2009 | Geiger |
| 2009/0216113 A1 * | 8/2009 | Meier ............... A61B 5/0002 600/424 |
| 2009/0312816 A1 | 12/2009 | Gross |
| 2010/0057204 A1 * | 3/2010 | Kadaba ............... A61F 2/442 623/17.12 |
| 2010/0100185 A1 * | 4/2010 | Trieu ............... A61F 2/4425 623/17.16 |
| 2010/0131067 A1 * | 5/2010 | Metcalf, Jr. ............... A61F 2/442 623/17.16 |
| 2010/0217369 A1 | 8/2010 | Gross |
| 2010/0324441 A1 | 12/2010 | Hargrove et al. |
| 2011/0046540 A1 | 2/2011 | Alterman et al. |
| 2011/0125158 A1 * | 5/2011 | Diwan ............... A61F 2/4657 606/93 |
| 2011/0160638 A1 | 6/2011 | Mauge et al. |
| 2011/0160797 A1 | 6/2011 | Makous et al. |
| 2012/0203307 A1 | 8/2012 | Schroeppel et al. |
| 2013/0066392 A1 | 3/2013 | Simon et al. |
| 2013/0102952 A1 | 4/2013 | Gross |
| 2013/0166006 A1 | 6/2013 | Williams |
| 2014/0058189 A1 | 2/2014 | Stubbeman |
| 2014/0088672 A1 | 3/2014 | Bedenbaugh |
| 2014/0207224 A1 | 7/2014 | Simon |
| 2014/0257168 A1 | 9/2014 | Gill |
| 2014/0324128 A1 | 10/2014 | Gross |
| 2015/0011927 A1 | 1/2015 | Hua |
| 2015/0119898 A1 | 4/2015 | Desalles et al. |
| 2016/0331970 A1 | 11/2016 | Lozano |
| 2017/0007823 A1 | 1/2017 | Gross |
| 2017/0120053 A1 | 5/2017 | Fostick et al. |
| 2017/0182317 A1 | 6/2017 | Gross et al. |
| 2018/0071523 A1 * | 3/2018 | Gross ............... A61N 1/326 |

FOREIGN PATENT DOCUMENTS

| | | |
|---|---|---|
| WO | 01/85027 | 11/2001 |
| WO | 2001/085094 | 11/2001 |
| WO | 2004/066903 | 8/2004 |
| WO | 2005/105053 | 11/2005 |
| WO | 2006/064502 | 6/2006 |
| WO | 2006/064503 | 6/2006 |
| WO | 2006/090397 | 8/2006 |
| WO | 2006/123346 | 11/2006 |
| WO | 2008/007369 | 1/2008 |
| WO | 2008/084477 | 7/2008 |
| WO | 2017/006327 | 1/2017 |
| WO | 2017/072769 | 5/2017 |

OTHER PUBLICATIONS

De La Torre JC, "Vascular Basis of Alzheimer's Pathogensis," Ann NY Acad Sci. 977:196-215 (Nov. 2002).

Weller Ro et al, "Perivascular Drainage of Amyloid-b Peptides from the Brain and Its Failure in Cerebral Amyloid Angiopathy and Alzheimer's Disease," Brain Pathology 18 (Apr. 2008) 253-266.

Brief PubMed search for metal ions in Alzheimers.

An Office Action dated Sep. 27, 2016, which issued during the prosecution of U.S. Appl. No. 14/926,705.

An International Search Report and a Written Opinion both dated Aug. 7, 2008, which issued during the prosecution of Applicant's PCT/IL2007/000865.

An Office Action dated Mar. 29, 2013, which issued during the prosecution of U.S. Appl. No. 12/373,306.

(56) References Cited

OTHER PUBLICATIONS

An Office Action dated Oct. 31, 2011, which issued during the prosecution of U.S. Appl. No. 12/373,306.
An Office Action dated Oct. 1, 2012, which issued during the prosecution of U.S. Appl. No. 12/373,306.
Notice of Allowance dated Jul. 24, 2013, which issued during the prosecution of U.S. Appl. No. 12/373,306.
An Office Action dated Apr. 11, 2013, which issued during the prosecution of U.S. Appl. No. 13/663,757.
Notice of Allowance dated Oct. 28, 2013, which issued during the prosecution of U.S. Appl. No. 13/663,757.
Elixmann IM et al., "In-vitro evaluation of a drainage catheter with integrated bioimpedance electrodes to determine ventricular size," Biomed Tech 2013; 58 (Suppl. 1) Sep. 2013 (2 pages total).
An Office Action dated Aug. 31, 2015, which issued during the prosecution of U.S. Appl. No. 13/872,794.
An Applicant Initiated Interview Summary dated Dec. 14, 2015, which issued during the prosecution of U.S. Appl. No. 13/872,794.
An Office Action dated Feb. 3, 2016, which issued during the prosecution of U.S. Appl. No. 13/872,794.
Notice of Allowance dated Dec. 9, 2016, which issued during the prosecution of U.S. Appl. No. 14/794,739.
An Applicant Initiated Interview Summary dated Feb. 25, 2016, which issued during the prosecution of U.S. Appl. No. 13/872,794.
An Office Action dated Jun. 15, 2016, which issued during the prosecution of U.S. Appl. No. 13/872,794.
An International Search Report and a Written Opinion both dated Oct. 20, 2016, which issued during the prosecution of Applicant's PCT/IL2016/050728.
U.S. Appl. No. 60/830,717, filed Jul. 12, 2006.
Vernengo J, "Injectable Bioadhesive Hydrogels for Nucleus Pulposus Replacement and Repair of the Damaged Intervertebral Disc: A Thesis," Drexel University (Jan. 2007).
Cheung KMC et al., "Intervertebral disc regeneration by use of autologous mesenchymal stem cells, an experimental model in rabbits," Abstract from the SRS 2004 Annual Meeting.
Freemont TJ et al., "Degeneration of intervertebral discs: current understanding of cellular and molecular events, and implications for novel therapies," Expert Reviews in Molecular Biology, Mar. 29, 2001 (Cambridge University Press).
Urban JPG et al., "The nucleus of the intervertebral disc from development to degeneration," American Zoologist 40(1): 53-61 (2000).
Restriction Requirement dated Sep. 12, 2011, which issued during the prosecution of U.S. Appl. No. 12/373,306.
An International Preliminary Report on Patentability dated Apr. 7, 2009, which issued during the prosecution of Applicant's PCT/IL2007/000865.
An International Preliminary Report on Patentability dated Dec. 22, 2009, which issued during the prosecution of Applicant's PCT/IL2008/000038.
An International Search Report and a Written Opinion both dated Sep. 2, 2008, which issued during the prosecution of Applicant's PCT/IL2008/000038.
An Office Action dated Jan. 16, 2015, which issued during the prosecution of U.S. Appl. No. 13/872,794.
Loutzenhiser, "Membrane Potential measurements in renal afferent and efferent arterioles: actions of Angiotensin II", AJP—Renal Physiol Aug. 1, 1997 vol. 273 No. 2 F307-F314.
Iatridis JC et al., "Influence of fixed charge density magnitude and distribution on the intervertebral disc: applications of a poroelastic and chemical electric (PEACE) model," J Biomech Eng. 125(1):12-24 (Feb. 2003).
"Implanting ultrathin electrodes in soft tissue," https://www.youtube.com/watch?v=FaBYQ68JIM8&spfreload=10, Published on Oct. 10, 2014 (excerpts from video).
Service RF, "Electric fields deliver drugs into tumors," http://news.sciencemag.org, Feb. 4, 2015.
Dao-Sheng Liu et al., "Activation of Na+ and K+ Pumping Modes of (Na,K)-ATPase by an Oscillating Electric Field," The Journal of Biological Chemistry, vol. 265. No. 13, May 5, 1990.(pp. 7260-7267).
An International Search Report and a Written Opinion both dated Jan. 26, 2017, which issued during the prosecution of Applicant's PCT/IL2016/051161.
An International Search Report and a Written Opinion both dated Mar. 10, 2017, which issued during the prosecution of Applicant's PCT/IL2016/051363.
An Office Action dated May 26, 2017, which issued during the prosecution of U.S. Appl. No. 15/453,290.
Notice of Allowance dated Jul. 24, 2017, which issued during the prosecution of U.S. Appl. No. 14/982,187.
Notice of Allowance dated Dec. 13, 2017, which issued during the prosecution of U.S. Appl. No. 15/263,910.
Corrected Notice of Allowability dated Jan. 3, 2018, which issued during the prosecution of U.S. Appl. No. 15/263,910.
An Office Action dated Apr. 25, 2018, which issued during the prosecution of U.S. Appl. No. 15/637,330.
An Invitation to pay additional fees dated Dec. 12, 2017, which issued during the prosecution of Applicant's PCT/IL2017/051032.
An International Search Report and a Written Opinion both dated Feb. 12, 2018, which issued during the prosecution of Applicant's PCT/IL2017/051032.
"ActivL® Artificial Disc" Patient Information, Aesculap Implant Systems, LLC, Jun. 2015, pp. 1-49.
"Hydropneumatic suspension," Wikipedia, downloaded May 19, 2019 from url https://en.wikipedia.org/wiki/Hydropneumatic_suspension, pp. 1-11.
"Charite Artificial Disc Patient Information", DePuy Spine, Inc., Oct. 2004, pp. 34-41.
"ProDisc C Disc Replacement. For single level spinal arthroplasty from C3 to C7. Technique Guide", Centinel Spine, Sep. 2017, pp. 1-32.
"M6-C Artificial Cervical Disc, The Natural Choice for Cervical Disc Replacement", Orthofix Holdings, Inc., Mar. 2019, pp. 1-6.
Gornet, Matthew F. et al., "MAVERICK Total Disc Replacement," Plastric Surgery Key, https://plasticsurgerykey.com/maverick-total-disc-replacement/, downloaded from url on Dec. 1, 2019, pp. 1-7.
Lauweryns, Philippe, "Design and Surgical Technique of the FlexiCore Lumbar Artificial Disc," Neupsy Key, https://neupsykey.com/design-and-surgical-technique-of-the-flexicore-lumbar-artificial-disc/, downloaded from url on Dec. 1, 2019, pp. 1-3.
"Kineflex Lumbar Disc", Southern Medical, http://www.southmed.co.za/kineflex-lumbar-disc-72, downloaded from url on Dec. 2, 2019, pp. 1-2.
Szpalski M et al., "Spine arthroplasty: a historical review," Eur Spine J, vol. 11, Suppl. 2, 2002, pp. S65-S84.

\* cited by examiner

HYDROPNEUMATIC ARTIFICIAL INTERVERTEBRAL DISC

FIELD OF THE APPLICATION

The present invention relates generally to therapeutic surgical techniques, and specifically to apparatus and methods for artificial disc replacement.

BACKGROUND OF THE APPLICATION

The intervertebral discs form cartilaginous joints between the end plates of vertebrae to provide shock absorption. Artificial disc replacement (ADR), also known as total disc replacement (TDR), is a surgical procedure in which degenerated intervertebral discs in the spinal column are replaced with artificial devices in the lumbar (lower) or cervical (upper) spine. The procedure is used to treat chronic, severe low back pain and cervical pain resulting from degenerative disc disease.

The activL® Artificial Disc (Aesculap Implant Systems, LLC, Center Valley, Pa., USA) for one-level lumbar use is a weight-bearing modular implant consisting of two endplates and one polyethylene inlay and is intended as an alternative to fusion. The activL Artificial Disc consists of two endplates made of a mix of metals commonly used in spine surgery (cobalt-chromium metal alloy with a titanium coating) and a polyethylene insert that fits between the two endplates. The plastic insert is flat on the bottom and round on the top and is designed to move as the patient moves during daily activities. The two endplates are held to the top and bottom surfaces of the involved vertebrae, and the plastic insert fits between them. The activL Artificial Disc is designed to allow motion at the treated level of the spine as the plastic insert can move front to back within the metal endplates but not side to side.

U.S. Pat. No. 8,577,469 to Gross, which is assigned to the assignee of the present application and is incorporated herein by reference, describes apparatus for treating an intervertebral disc of a subject. The apparatus includes a first electrode, configured to be inserted into a nucleus pulposus of the disc, and a second electrode, configured to be placed outside of the nucleus pulposus, in a vicinity of the nucleus pulposus. A control unit is configured to drive a current between the first and second electrodes, and to configure the current to electroosmotically drive fluid between inside and outside the nucleus pulposus. Other embodiments are also described.

SUMMARY OF THE APPLICATION

Some embodiments of the present invention provide a hydropneumatic artificial intervertebral disc (IVD), which is configured to imitate some aspects of the function of a natural, healthy IVD. The artificial IVD is typically configured to automatically regulate the pressure therein dynamically responsively to the subject's level of activity.

For some applications, the artificial IVD comprises two endplates having oppositely-facing outward surfaces configured to engage respective intervertebral surfaces of the spinal column; and a chamber, which is disposed between oppositely-facing inner surfaces of the two endplates, and which comprises a lateral wall comprising an electroosmotic membrane. The artificial IVD further comprises a plurality of exposed electrode surface, including (i) one or more intra-chamber exposed electrode surfaces, which are located within the chamber; and (ii) one or more extra-chamber exposed electrode surfaces, which are located outside the chamber, in a vicinity of the chamber.

Control circuitry is configured to drive at least one of the one or more intra-chamber exposed electrode surfaces and at least one of the one or more extra-chamber exposed electrode surfaces to electroosmotically drive liquid from outside the chamber to inside the chamber.

For some applications, the control circuitry is configured to drive at least two of the exposed electrode surfaces to generate a gas in the chamber by electrolysis of water of the liquid in the chamber.

For some of these applications, the control circuitry is configured to ascertain a level of motion of the artificial IVD, and to drive the at least two of the exposed electrode surfaces to generate the gas at least in part based on the ascertained level of motion. The sensed level of motion provides an indication of physical activity, such as physical exercise. The gas generated during elevated physical activity may provide better shock-absorption than liquid alone, because the gas is compressible. In addition, gas can be generated in the chamber more quickly than liquid can be driven from outside the chamber to inside the chamber. This quicker generation may allow a relatively quick increase (typically within minutes) in the pressure in the chamber upon commencement of increased physical activity, in order to provide an appropriate level of cushioning by the artificial IVD during the increased physical activity.

There is therefore provided, in accordance with an application of the present invention, apparatus including:

(a) an artificial intervertebral disc (IVD) for replacement of a degenerated intervertebral disc in a spinal column of a subject, the artificial IVD including:

two endplates having oppositely-facing outward surfaces configured to engage respective intervertebral surfaces of the spinal column;

a chamber, which is disposed between oppositely-facing inner surfaces of the two endplates, and which includes a lateral wall including an electroosmotic membrane;

a plurality of exposed electrode surface, including (i) one or more intra-chamber exposed electrode surfaces, which are located within the chamber; and (ii) one or more extra-chamber exposed electrode surfaces, which are located outside the chamber, in a vicinity of the chamber; and (b) control circuitry, which is configured to drive at least one of the one or more intra-chamber exposed electrode surfaces and at least one of the one or more extra-chamber exposed electrode surfaces to electroosmotically drive liquid from outside the chamber to inside the chamber.

For some applications, the control circuitry is configured to drive the at least one of the one or more intra-chamber exposed electrode surfaces and the at least one of the one or more extra-chamber exposed electrode surfaces to electroosmotically drive the liquid from outside the chamber to inside the chamber by configuring the at least one of the intra-chamber exposed electrode surface to be a cathode, and the at least one of the extra-chamber exposed electrode surface to be an anode.

For some applications, the control circuitry is disposed within the artificial IVD.

For some applications, the artificial IVD further includes a wire coil, which is configured to receive electromagnetically transmitted energy for electroosmotically driving the liquid from outside the chamber to inside the chamber.

For some applications:

the artificial IVD further includes a pressure sensor, which is arranged to sense a pressure within the chamber, and the control circuitry is configured to drive the at least one of the one or more intra-chamber exposed electrode surfaces and the at least one of the one or more extra-chamber exposed electrode surfaces to electroosmotically drive the liquid at least in part based on the sensed pressure.

For some applications, the control circuitry is configured to drive the at least one of the one or more intra-chamber exposed electrode surfaces and the at least one of the one or more extra-chamber exposed electrode surfaces to electroosmotically drive the liquid by applying a voltage of no more than 1.2 V between the at least one of the one or more intra-chamber exposed electrode surfaces and the at least one of the one or more extra-chamber exposed electrode surfaces.

For some applications, the control circuitry is configured to drive at least two of the exposed electrode surfaces to generate a gas in the chamber by electrolysis of water of the liquid in the chamber.

For some applications:
the artificial IVD includes a plurality of the intra-chamber exposed electrode surfaces, and
the control circuitry is configured to drive at least two of the intra-chamber exposed electrode surfaces to generate the gas in the chamber by electrolysis of water of the liquid in the chamber.

For some applications, the at least one of the one or more intra-chamber exposed electrode surfaces driven to electroosmotically drive the liquid is at least one of the at least two of the intra-chamber exposed electrode surfaces driven to generate the gas.

For some applications, the control circuitry is configured to drive at least one of the one or more intra-chamber exposed electrode surfaces and at least one of the one or more extra-chamber exposed electrode surfaces to generate the gas in the chamber by electrolysis of water of the liquid in the chamber.

For some applications, the control circuitry is configured to drive the at least one of the one or more intra-chamber exposed electrode surfaces and the at least one of the one or more extra-chamber exposed electrode surfaces to generate the gas in the chamber by configuring the at least one of the intra-chamber exposed electrode surface to be an anode, and the at least one of the extra-chamber exposed electrode surface to be an cathode.

For some applications, the control circuitry is configured to:
ascertain a level of motion of the artificial IVD, and
drive the at least two of the exposed electrode surfaces to generate the gas at least in part based on the ascertained level of motion.

For some applications:
the artificial IVD further includes a motion sensor, which is arranged to sense the level of motion of the artificial IVD, and
the control circuitry is configured to ascertain the level of motion based on the level of motion sensed by the motion sensor.

For some applications:
the artificial IVD further includes a pressure sensor, which is arranged to sense a pressure within the chamber, and
the control circuitry is configured to ascertain the level of motion based on a rate of change of the sensed pressure within the chamber.

For some applications:
the artificial IVD further includes a pressure sensor, which is arranged to sense a pressure within the chamber, and the control circuitry is configured to drive, at least in part based on the sensed pressure, the at least two of the exposed electrode surfaces to generate the gas.

For some applications, the control circuitry is configured to drive, at least in part based on the sensed pressure and a target pressure, the at least two of the exposed electrode surfaces to generate the gas.

For some applications, the control circuitry is configured to:
ascertain a level of motion of the artificial IVD, and
drive, at least in part based on the sensed pressure and at least in part based on the ascertained level of motion, the at least two of the exposed electrode surfaces to generate the gas.

For some applications:
the control circuitry is configured to set a target pressure within the chamber at least in part based on the ascertained level of motion, and
the control circuitry is configured to drive, at least in part based on the sensed pressure and the target pressure, the at least two of the exposed electrode surfaces to generate the gas.

For some applications, the control circuitry is configured to drive the at least two of the exposed electrode surfaces to generate a gas by applying a voltage of at least 1.3 V between the at least two of the exposed electrode surfaces.

For some applications, the artificial IVD further includes a flexible support, which is disposed between the two endplates and regulates relative movement of the two endplates.

For some applications, the chamber is annular and surrounds the flexible support.

For some applications, the flexible support is shaped so as to define a compartment. For some applications, the control circuitry is located within the compartment of the flexible support. For some applications, the artificial IVD further includes a wire coil, which is located within the compartment of the flexible support, and is configured to receive electromagnetically transmitted energy for electroosmotically driving the liquid from outside the chamber to inside the chamber. For some applications, the artificial IVD further includes a motion sensor, which is located within the compartment of the flexible support.

For some applications, the control circuitry is configured to:
ascertain a level of motion of the artificial IVD, and
drive the at least one of the one or more intra-chamber exposed electrode surfaces and the at least one of the one or more extra-chamber exposed electrode surfaces to electroosmotically drive the liquid at least in part based on the ascertained level of motion.

For some applications:
the artificial IVD further includes a motion sensor, which is arranged to sense the level of motion of the artificial IVD, and
the control circuitry is configured to ascertain the level of motion based on the level of motion sensed by the motion sensor.

For some applications:
the artificial IVD further includes a pressure sensor, which is arranged to sense a pressure within the chamber, and
the control circuitry is configured to ascertain the level of motion based on a rate of change of the sensed pressure within the chamber.

For some applications, the artificial IVD further includes a band, which is disposed outside and surrounding the lateral wall of the chamber, and which is configured to constrain lateral expansion of the chamber.

For some applications, the band includes a metal, and serves as the one or more extra-chamber exposed electrode surfaces.

For some applications, a system is provided including the artificial IVD and the circuitry, and further including a delivery shaft in which the artificial IVD is removably disposed in a compressed configuration. For some applications, when the artificial IVD is in the collapsed configuration, the outward surface of one of the two endplates is concave when viewed from outside the artificial IVD and the outward surface of the other of the two endplates is convex when viewed from outside the artificial IVD.

There is further provided, in accordance with an application of the present invention, a method of treating a spinal column of a subject, the method including:

removing a degenerated intervertebral disc from between intervertebral surfaces of the spinal column;

implanting an artificial intervertebral disc (IVD) such that (a) oppositely-facing outward surfaces of two endplates of the artificial IVD engage the intervertebral surfaces of the spinal column, respectively, and (b) one or more extra-chamber exposed electrode surfaces of the artificial IVD are located outside the chamber, in a vicinity of the chamber, wherein the artificial IVD further includes (a) a chamber, which is disposed between oppositely-facing inner surfaces of the two endplates, and which includes a lateral wall including an electroosmotic membrane, and (b) one or more intra-chamber exposed electrode surfaces, which are located within the chamber; and activating control circuitry to drive at least one of the intra-chamber exposed electrode surfaces and at least one of the extra-chamber exposed electrode surfaces to electroosmotically drive liquid from outside the chamber to inside the chamber.

For some applications, implanting the artificial IVD includes implanting the artificial IVD while the chamber is deflated. For some applications, implanting the artificial IVD while the chamber is deflated includes implanting the artificial IVD while the outward surface of one of the two endplates is concave when viewed from outside the artificial IVD and the outward surface of the other of the two endplates is convex when viewed from outside the artificial IVD. For some applications, implanting the artificial IVD while the chamber is deflated includes implanting the artificial IVD while the artificial IVD is in a collapsed configuration removably disposed in a delivery shaft.

For some applications, the artificial IVD further includes a flexible support, which is disposed between the two endplates and regulates relative movement of the two endplates.

The present invention will be more fully understood from the following detailed description of embodiments thereof, taken together with the drawings, in which:

DETAILED DESCRIPTION OF APPLICATIONS

Figure 1:
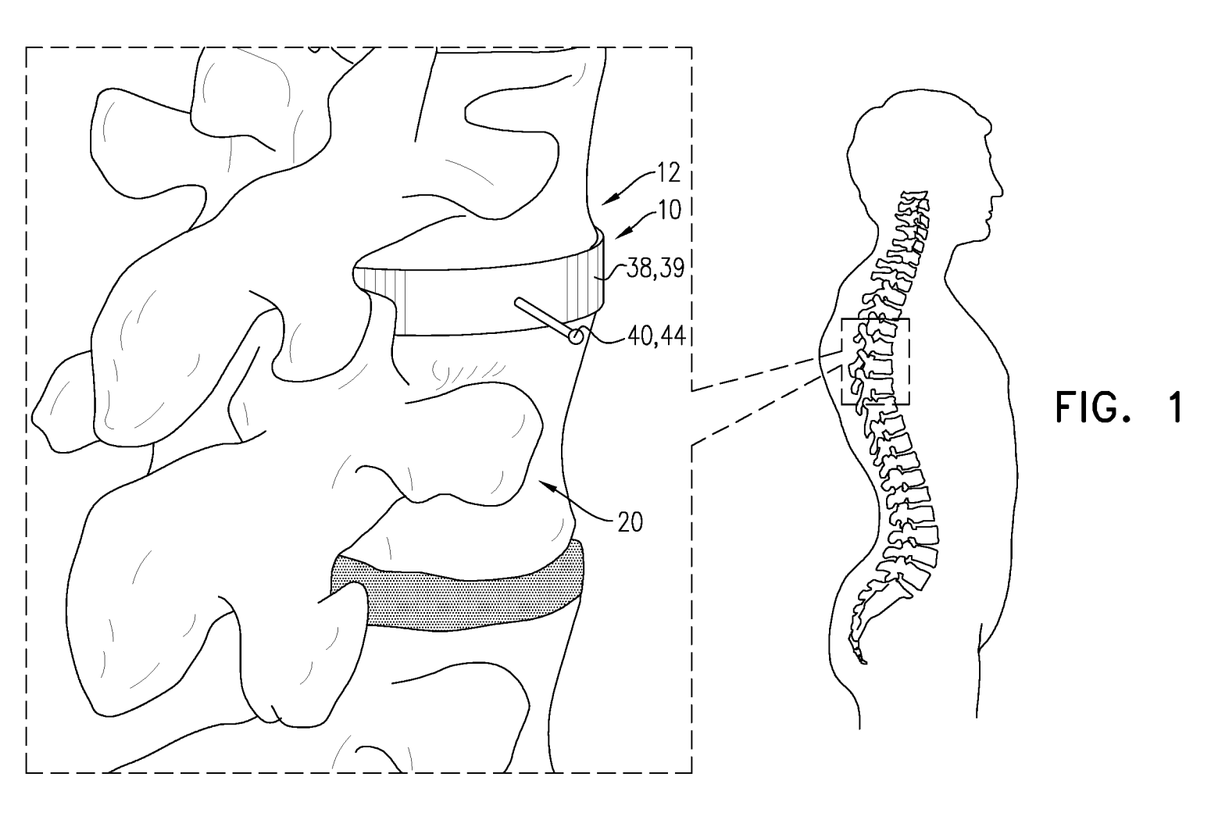
FIG. 1 is a schematic illustration of an artificial intervertebral disc (IVD) system, comprising an artificial intervertebral disc (IVD) implanted in a spinal column of a subject, in accordance with an application of the present invention.

FIG. 1 is a schematic illustration of an artificial intervertebral disc (IVD) system 10, comprising an artificial intervertebral disc (IVD) 12 implanted in a spinal column 20 of a subject, in accordance with an application of the present invention. Artificial IVD system 10 is used to treat spinal column 20 by replacing a degenerated intervertebral disc.

Figure 2A:
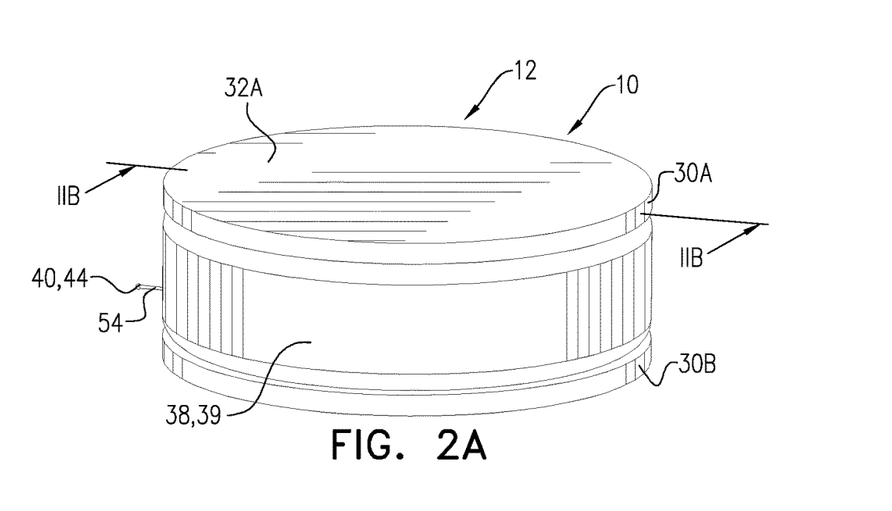
FIGS. 2A-C are schematic illustrations of the artificial IVD system of FIG. 1, in accordance with an application of the present invention.
Figure 2B:
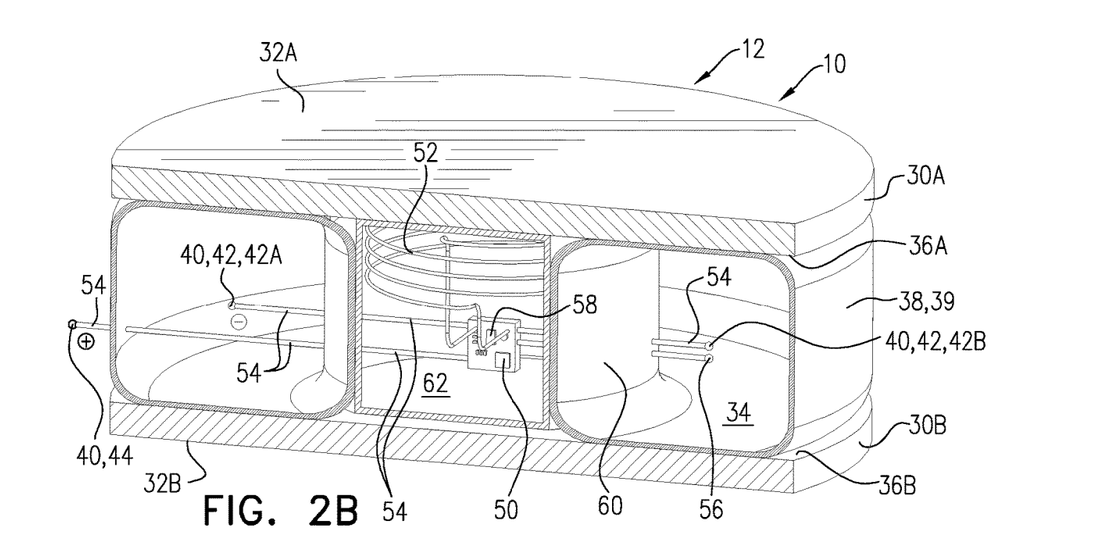
Figure 2C:
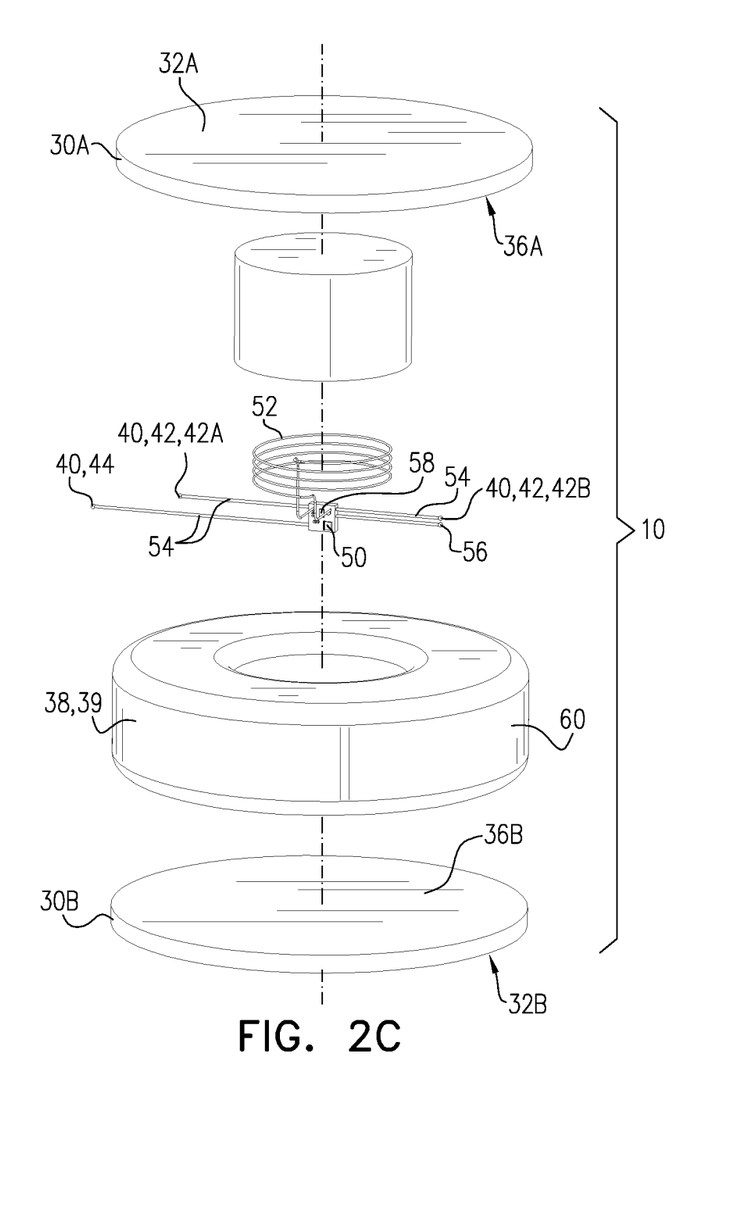

Reference is made to FIGS. 2A-C, which are schematic illustrations of artificial IVD system 10, in accordance with an application of the present invention. FIG. 2B is a cross-sectional view of artificial IVD system 10, and FIG. 2C is an exploded view showing components of artificial IVD system 10.

Artificial IVD 12 comprises:
two endplates 30A and 30B having oppositely-facing outward surfaces 32A and 32B configured to engage respective intervertebral surfaces of spinal column 20; for example, endplates 30A and 30B may comprise a metal, such as Nitinol;
a chamber 34, which is disposed between oppositely-facing inner surfaces 36A and 36B of the two endplates 30A and 30B, and which comprises a lateral wall 38 comprising an electroosmotic membrane 39; biocompatible osmotic membranes are well known in the art; typically, electroosmotic membrane 39 is hydrophobic; and
a plurality of exposed electrode surfaces 40.
The plurality of exposed electrode surfaces 40 includes:
one or more intra-chamber exposed electrode surfaces 42, which are located within chamber 34; and
one or more extra-chamber exposed electrode surfaces 44, which are located outside chamber 34, in a vicinity of chamber 34.

Artificial IVD system 10 further comprises control circuitry 50, which is configured to drive at least one 42A of the one or more intra-chamber exposed electrode surfaces 42 and at least one of the one or more extra-chamber exposed electrode surfaces 44 to electroosmotically drive liquid from outside chamber 34 to inside chamber 34. Typically, for driving the liquid, control circuitry 50 is configured to configure the at least one 42A of the intra-chamber exposed electrode surfaces 42 to be a cathode, and the at least one of the extra-chamber exposed electrode surfaces 44 to be an anode.

For some applications, control circuitry 50 is configured to drive the at least one 42A of the one or more intra-chamber exposed electrode surfaces 42 and the at least one of the one or more extra-chamber exposed electrode surfaces 44 to electroosmotically drive the liquid by applying a voltage of no more than 1.2 V, for example, pulses of 1 V, between the at least one 42A of the one or more intra-chamber exposed electrode surfaces 42 and the at least one of the one or more extra-chamber exposed electrode surfaces 44. Alternatively or additionally, for some applications, control circuitry 50 is configured to apply the current with a low frequency, such as between 0.5 and 2 Hz. This frequency is typically insufficient to stimulate a nerve, which typically requires about 5-20 Hz. Further alternatively or additionally, for some applications, control circuitry 50 is configured to apply direct current, e.g., with an average amplitude of between 1 and 10 mA. Alternatively or additionally, for some applications, the duty cycle is typically low, e.g., at least 5%, less than 40% (e.g., less than 30%), and/or between 5% and 40%, such as between 5% and 30%, for example, between 5% and 15%, such as 10%. Typically, control circuitry 50 is activated to apply the current monophasically, in order to drive the liquid in only one direction. In contrast, nerve stimulators typically apply a few volts, and do not cause electrolysis because the applied signal is biphasic. For some applications, the control unit is configured to apply the direct current as a series of pulses, e.g., having a pulse duration of at least 1 second, such as at least 10 seconds, e.g., at least one minute.

Figure 3A:
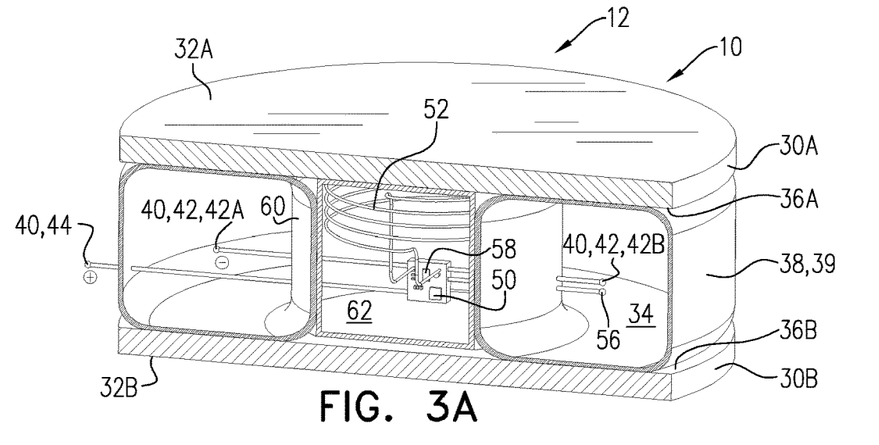
FIGS. 3A-C are schematic illustrations of the artificial IVD system of FIG. 1 at different levels of filling, in accordance with an application of the present invention.
Figure 3B:
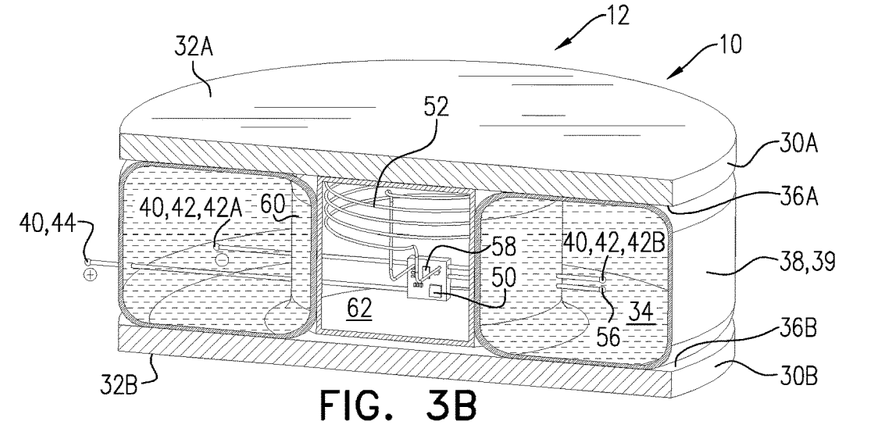
Figure 3C:
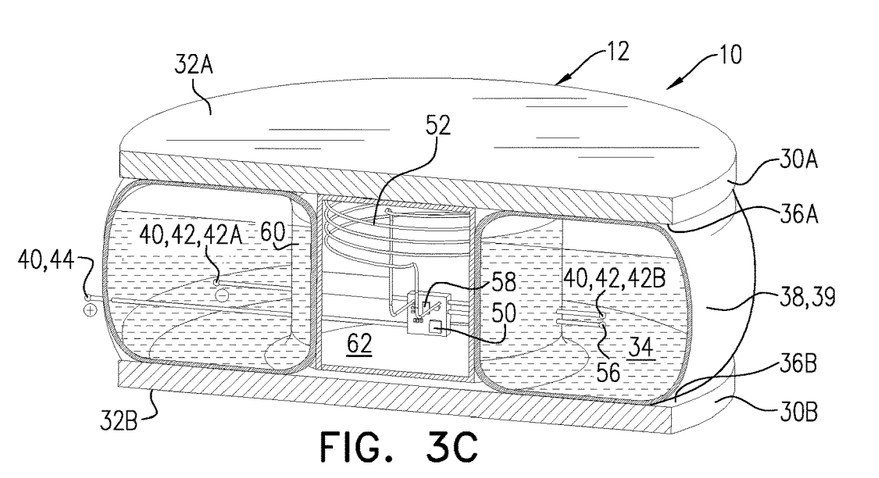

For some applications, control circuitry 50 is disposed within artificial IVD 12, as shown in FIGS. 2B-C (and FIGS. 3A-C). For other applications, control circuitry 50 is disposed in an external control unit 90, such as described hereinbelow with reference to FIG. 4.

Typically, lateral wall 38 (including electroosmotic membrane 39 thereof) is elastic; for example, lateral wall 38 may comprise a polymer, such as an elastomer. Optionally, lateral wall 38 is reinforced by band 180, described hereinbelow with reference to FIG. 6. This elasticity may help accommodate an increase in volume of chamber 34 (for example, lateral wall 38 may bulge laterally outward to accommodate at least part of an increase in volume in chamber 34, as shown in FIG. 3C), which may provide more flexibility to artificial IVD 12. In addition, endplates 30A and 30B may separate somewhat axially from each other in order to partially accommodate the increase in volume in chamber 34. Typically, a total volume of chamber 34 increases by no more than 10% during use of artificial IVD system 10.

For some applications, such as of the configurations shown in the figures, the one or more intra-chamber exposed electrode surfaces 42 and the one or more extra-chamber exposed electrode surfaces 44 are supported by respective support structures 54 (labeled in FIG. 2B), e.g., comprising respective insulated wires. Alternatively or additionally, for other applications, the one or more intra-chamber exposed electrode surfaces 42 and/or the one or more extra-chamber exposed electrode surfaces 44 comprise respective conductive coatings on the internal and/or external surfaces, respectively, of lateral wall 38 of chamber 34 and/or other internal and/or external surfaces of artificial IVD 12 (configuration not shown). Further alternatively or additionally, for some applications in which artificial IVD 12 comprises band 180, as described hereinbelow with reference to FIG. 6, band 180 serves as the one or more extra-chamber exposed electrode surfaces 44 of artificial IVD 12 (configuration not shown).

For some applications, artificial IVD 12 further comprises a wire coil 52, which is configured to receive electromagnetically transmitted energy for electroosmotically driving the liquid from outside chamber 34 to inside chamber 34 (and, optionally, generating the gas, as described hereinbelow). For example, external control unit 90, described hereinbelow with reference to FIG. 4, may comprise a transmitter for electromagnetically transmitting energy (optionally connected to a smartphone).

For some applications, control circuitry 50 is configured to drive at least two of exposed electrode surfaces 40 to generate a gas in chamber 34 by electrolysis of water of the liquid in chamber 34.

For some of these applications, artificial IVD 12 comprises a plurality of the intra-chamber exposed electrode surfaces 42, and control circuitry 50 is configured to drive at least two 42A, 42B of the intra-chamber of exposed electrode surfaces 42 to generate the gas in chamber 34 by electrolysis of water of the liquid in chamber 34 to generate oxygen and hydrogen in the chamber. For some of these applications, the at least one 42A of the one or more intra-chamber exposed electrode surfaces 42 driven to electroosmotically drive the liquid is at least one 42A of the at least two 42A, 42B of the intra-chamber exposed electrode surfaces 42 driven to generate the gas, as shown in FIGS. 2B and 2C (and FIGS. 3A-C). Alternatively, intra-chamber exposed electrode surfaces 42 include at least a third intra-chamber exposed electrode surface 42, which is driven, along with electrode surface 42B, to generate the gas, and electrode surface 42A is only driven to electroosmotically drive the liquid.

Alternatively, for other applications, control circuitry 50 is configured to drive at least one of the one or more intra-chamber exposed electrode surfaces 42 and at least one of the one or more extra-chamber exposed electrode surfaces 44 to generate the gas in the chamber by electrolysis of water of the liquid in the chamber. Typically, control circuitry 50 is configured to configure the at least one of the intra-chamber exposed electrode surfaces 42 to be an anode, and the at least one of the extra-chamber exposed electrode surfaces 44 to be a cathode, such that the electrolysis generates oxygen of the gas inside the chamber and hydrogen of the gas outside the chamber. Generation of the oxygen inside the chamber may be more efficient than generation of the hydrogen inside the chamber, because oxygen molecules are larger than hydrogen molecules and therefore less permeable through lateral wall 38 of chamber 34.

For some applications, control circuitry 50 is configured to drive the at least two of exposed electrode surfaces 40 to generate the gas by applying a voltage of at least 1.3 V, for example, pulses of 1.3-5 V, between the at least two of exposed electrode surfaces 40. Further alternatively or additionally, for some applications, control circuitry 50 is configured to apply direct current, e.g., with an average amplitude of at least 2 mA, no more than 20 mA, and/or between 2 and 20 mA.

For some applications, artificial IVD 12 further comprises a pressure sensor 56, which is arranged to sense a pressure within chamber 34. Control circuitry 50 is configured to drive the at least one 42A of the one or more intra-chamber exposed electrode surfaces 42 and the at least one of the one or more extra-chamber exposed electrode surfaces 44 to electroosmotically drive the liquid at least in part based on the sensed pressure. For example, control circuitry 50 may be configured to drive the at least one 42A of the one or more intra-chamber exposed electrode surfaces 42 and the at least one of the one or more extra-chamber exposed electrode surfaces 44 to electroosmotically drive the liquid when the pressure falls below a threshold level, in order to maintain at least a minimum level of pressure in chamber 34. Optionally, the threshold pressure may be dependent on the circadian cycle of the subject, and/or on the activity level of the subject.

For some applications in which control circuitry 50 is configured to additionally drive at least two of the exposed electrode surfaces 40 to generate the gas, as described hereinabove, control circuitry 50 is configured to drive the at least two of the exposed electrode surfaces 40 to generate the gas at least in part based on the sensed pressure.

Optionally, control circuitry 50 is configured to drive any of the above-mentioned pairs of electrodes at least in part based on the sensed pressure and a target pressure, so as to increase the pressure toward the target pressure.

For some applications, control circuitry 50 is configured to ascertain a level of motion of artificial IVD 12. The sensed level of motion provides an indication of physical activity, such as physical exercise. Increased motion may reflect an elevated level of physical activity. For some of these applications, artificial IVD 12 further comprises a motion sensor 58 (e.g., an accelerometer), which is arranged to sense a level of motion of artificial IVD 12, and control circuitry 50 is configured to ascertain the level of motion based on the level of motion sensed by motion sensor 58. Alternatively or additionally, for some of these applications, control circuitry 50 is configured to ascertain the level of motion based on a rate of change of the sensed pressure (dP/dt) within the chamber by pressure sensor 56. Alternatively, for some of these applications, control circuitry 50 is configured to ascertain the level of motion based on another parameter of the sensed pressure, such as a measure of variability of the sensed pressure.

For some applications, control circuitry 50 is configured to drive the at least one 42A of the one or more intra-chamber exposed electrode surfaces 42 and the at least one of the one or more extra-chamber exposed electrode surfaces 44 to electroosmotically drive the liquid at least in part based on the ascertained level of motion.

For some applications in which control circuitry 50 is configured to additionally drive at least two of the exposed electrode surfaces 40 to generate the gas, as described hereinabove, control circuitry 50 is configured to drive the at least two of the exposed electrode surfaces 40 to generate the gas at least in part based on the ascertained level of motion. Typically, control circuitry 50 is configured to commence the driving and/or increase a level of the driving responsively to an increased ascertained level of motion.

The gas generated during elevated physical activity may provide better shock-absorption than liquid alone, because the gas is compressible. In addition, gas can be generated in chamber 34 more quickly than liquid can be driven from outside chamber 34 to inside chamber 34. This quicker generation may allow a relatively quick increase (typically within minutes) in the pressure in chamber 34 upon commencement of increased physical activity, in order to provide an appropriate level of cushioning by artificial IVD 12 during the increased physical activity. (Typically, the flexibility of lateral wall 38 provides some shock-absorption even before a substantial amount of gas is generated.)

For some applications, control circuitry 50 is configured to:
- sense whether the amount of liquid in chamber 34 is insufficient to allow hydrolysis because the at least two of the exposed electrode surfaces 40 are exposed to gas rather than liquid, and
- if the amount is insufficient, to (a) drive the at least one 42A of the one or more intra-chamber exposed electrode surfaces 42 and the at least one of the one or more extra-chamber exposed electrode surfaces 44 to electroosmotically drive the liquid into chamber 34 until there is sufficient liquid to allow hydrolysis, and/or (b) withhold driving the at least two of the exposed electrode surfaces 40 to generate the gas.

For example, the amount of liquid may become insufficient to allow hydrolysis if the subject exercises for long period of time and/or strenuously, which may cause chamber 34 to naturally lose fluid. Optionally, control circuitry 50 is configured to sense whether the amount of liquid in chamber 34 is insufficient to allow hydrolysis by sensing an impedance greater than a threshold level, indicative of gas rather than liquid in the chamber.

Typically, when the subject is at a low level of physical activity, such as during rest or sleep, in response to the low level of motion of artificial IVD 12 detected by motion sensor 58, control circuitry 50 does not drive the at least two exposed electrode surfaces 42 to generate gas. As a result, chamber 34 contains only liquid. Even liquid alone provides some shock-absorption, because chamber 34 changes shape in response to applied forces, like natural intervertebral discs. In some configurations, when chamber 34 entirely filled with liquid, chamber 34 shortens axially (i.e., vertically in the figures) and expands laterally when the chamber is axially squeezed between endplates 30A and 30B. This level of shock-absorption obviates the need for control circuitry 50 to constantly maintain some gas in chamber 34. Such constant maintenance of gas in chamber 34 would require nearly continuous generation of gas, because gas naturally leaks out of chamber 34. The techniques described above allow artificial IVD 22 to generate gas only on demand, e.g., in response to increased physical activity.

For some applications in which control circuitry 50 is configured to additionally drive at least two of the exposed electrode surfaces 40 to generate the gas, as described hereinabove, control circuitry 50 is configured to drive the at least two of the exposed electrode surfaces 40 to generate the gas at least in part based on the sensed pressure and at least in part based on the ascertained level of motion.

For some applications, control circuitry 50 is configured to set a target pressure within chamber 34 at least in part based on the sensed level of motion, and to drive the at least two of the exposed electrode surfaces 40 to generate the gas at least in part based on the sensed pressure and the target pressure.

For some applications, control circuitry 50 is configured to set the target pressure within chamber 34 to have a positive relationship with the sensed level of motion, i.e., to set the target pressure higher at greater sensed levels of motion. The resulting increased pressure within chamber 34 provides greater shock-absorption during increased physical activity.

For some applications, control circuitry 50 is configured to set a level of the driving in a feedback loop, so as to increase the sensed pressure to the target pressure.

Reference is now made to the following Table A. For some applications, control circuitry 50 is configured to (a) drive the at least one 42A of the one or more intra-chamber exposed electrode surfaces 42 and the at least one of the one or more extra-chamber exposed electrode surfaces 44 to electroosmotically drive the liquid ("Electroosmosis" in Table A) and/or (b) drive the at least two of the exposed electrode surfaces 40 to generate the gas ("Electrolysis" in Table A) as set forth in Table A:

TABLE A

| Inputs | | Control circuitry 50 drives | |
|---|---|---|---|
| Ascertained Level of Motion | Sensed Pressure | Electro-osmosis | Electrolysis |
| #1 Very low | Very low | On | Off |
| #2 Very low | Above medium | Off | Off |
| #3 Medium | Medium | On | Off |
| #4 High | Above medium | Off | On |
| #5 High | Low | On | On |

Thus, for example, if the subject has been lying in bed for several hours, it may be that the sensed dP/dt and the sensed pressure will both be very low. In such a case, control circuitry 50 may drive the at least one 42A of the one or more intra-chamber exposed electrode surfaces 42 and the at least one of the one or more extra-chamber exposed electrode surfaces 44 to electroosmotically drive the liquid into chamber 34 in order to achieve a sufficient ("above medium") level of pressure in the chamber. At that point, when the sensed pressure is sufficient, the electroosmosis is typically turned off (and the electrolysis remains off). This is reflected in Table A by the transition from Row #1 to Row #2.

In another example, if only a medium level of dP/dt is sensed (e.g., the subject is walking from the kitchen to the bedroom), and the sensed pressure is a little lower than desired, as reflected in Row #3, then control circuitry 50 may drive the at least one 42A of the one or more intra-chamber exposed electrode surfaces 42 and the at least one of the one or more extra-chamber exposed electrode surfaces 44 to electroosmotically drive the liquid into chamber 34 in order to achieve a sufficient ("above medium") level of pressure in the chamber.

However, if the sensed dP/dt is high and the sensed pressure is sufficient ("above medium"), as reflected in Row #4, e.g., the subject is engaging in exercise, then control circuitry 50 typically drives the at least two of the exposed electrode surfaces 40 to generate the gas in order to quickly respond to the exercise and maintain a desired level of shock absorbing to accommodate the subject's exercising.

Lastly, if the sensed dP/dt is high and the sensed pressure is low, as reflected in Row #5, e.g., the subject gets out of bed and immediately begins to exercise, then control circuitry 50 will typically initiate both electroosmosis and electrolysis, as described herein.

Alternatively, for some applications, control circuitry 50 is configured, when the sensed dP/dt and/or ascertained level of motion is high and the sensed pressure is low, to wait until the amount of liquid in the chamber is sufficient for allowing electrolysis before commencing driving the at least one 42A of the one or more intra-chamber exposed electrode surfaces 42 and the at least one of the one or more extra-chamber exposed electrode surfaces 44 to electroosmotically drive the liquid. Control circuitry 50 may sense the sufficiency of the liquid as described hereinabove.

For some applications, artificial IVD 12 further comprises a flexible support 60, which is disposed between the two endplates 30A and 30B and regulates relative movement of the two endplates 30A and 30B. For example, flexible support 60 may comprise a polymer, such as an elastomer. Flexible support 60 may be fixed to one or both of endplates 30A and 30B, or may be in direct or indirect physical contact with one or both of the endplates, without being fixed thereto.

For some applications, as shown in the figures, chamber 34 is annular and surrounds flexible support 60, which thus serves as a core. For some of these applications, flexible support 60 is shaped so as to define a compartment 62. One or more of the following elements may be located within compartment 62: control circuitry 50, wire coil 52, and/or motion sensor 58. Alternatively, for other applications, flexible support 60 may be annular and surround chamber 34, similar to the annulus of a natural IVD (configuration not shown).

Reference is now made to FIGS. 3A-C, which are schematic illustrations of artificial IVD system 10 at different levels of filling, in accordance with an application of the present invention.

FIG. 3A shows, for example, artificial IVD system 10 upon initial implantation, before control circuitry 50 drives liquid into chamber 34 and/or liquid has been injected into chamber 34, as described hereinbelow with reference to FIG. 5.

FIG. 3B shows, for example, artificial IVD system 10 during minimal physical activity of the subject, e.g., when the subject is resting or sleeping. In response to this low level of physical activity, control circuitry 50 has not driven the exposed electrode surfaces to generate the gas.

FIG. 3C shows, for example, artificial IVD system 10 during elevated physical activity, e.g., exercise, of the subject. In response to this elevated level of physical activity, control circuitry 50 has driven the exposed electrode surfaces to generate the gas (which may optionally increase the height of artificial IVD 12).

Figure 4:
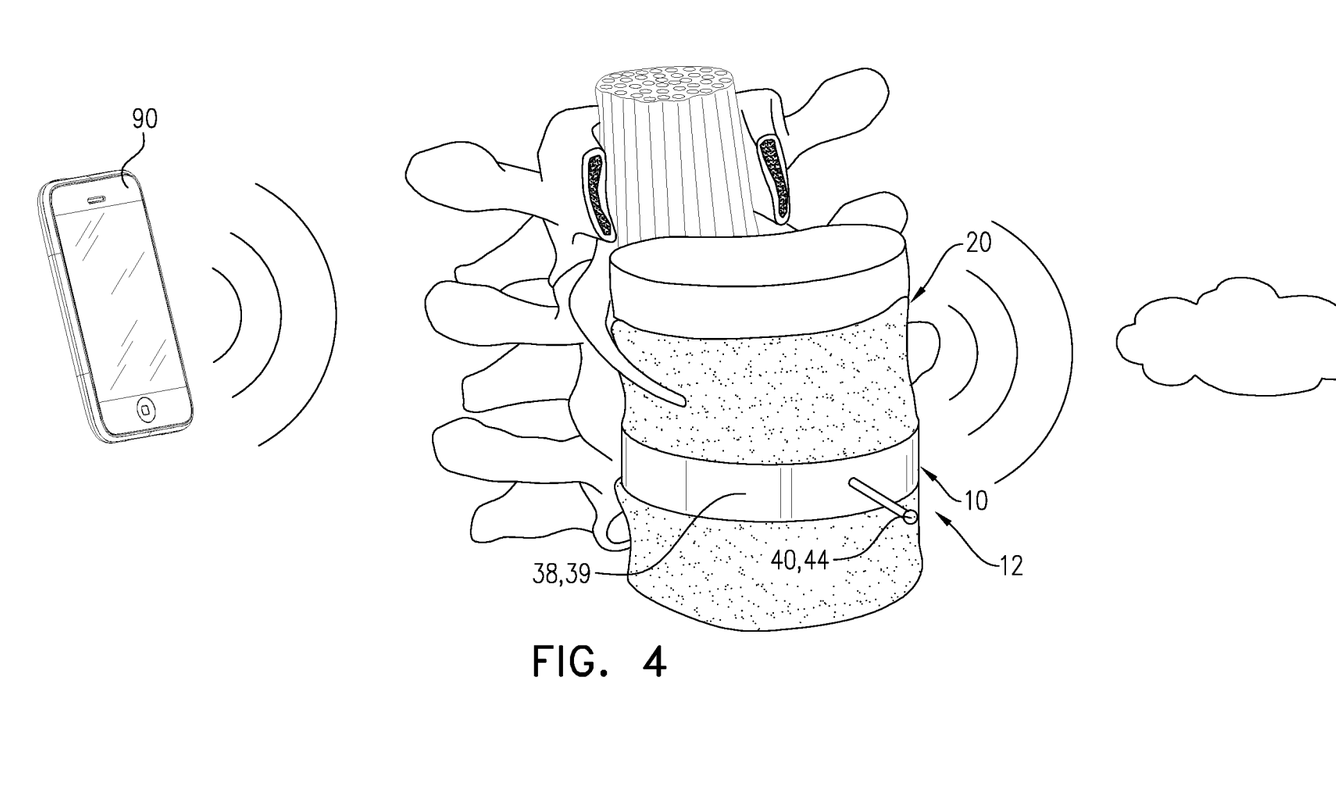
FIG. 4 is a schematic illustration of the artificial IVD system of FIG. 1 after implantation thereof, in accordance with an application of the present invention.

Reference is now made to FIG. 4, which is a schematic illustration of artificial IVD system 10 after implantation thereof, in accordance with an application of the present invention. After artificial IVD 12 has been implanted, control circuitry 50 is activated, typically by a healthcare worker, such as a physician, to provide the functions described herein. Activating control circuitry 50 may include configuring parameters and/or functions of control circuitry 50 (such as using a separate programmer or external control unit 90), or activating control circuitry 50 to perform functions pre-programmed in control circuitry 50. Control circuitry 50 typically comprises appropriate memory, processor(s), and hardware running software that is configured to provide the functionality of control circuitry 50 described herein. For example, external control unit 90 may comprise a conventional smartphone.

For some applications, control circuitry 50 is remotely programmable using external control unit 90, to match environmental conditions, lifestyle, and/or body type.

For some applications, control circuitry 50 is configured to provide the subject with control of activation of control circuitry 50, e.g., in response to activity or pain. For example, the control may be provided from the subject's telephone (e.g., smartphone) or another electronic device.

For some applications, control circuitry 50 is configured to drive the exposed electrode surfaces to electroosmotically drive the liquid and/or generate the gas based on a circadian cycle of the subject. For example, control circuitry 50 may be configured to drive the liquid and/or generate the gas during the daytime, i.e., over the course of the day, when the subject is more active (and/or when the subject is sensed to be active, as described hereinabove). Further alternatively, control circuitry 50 is activated generally constantly, or regularly intermittently (e.g., one hour on/one hour off).

For some applications, all or a portion of control circuitry 50 is disposed in external control unit 90, rather than within artificial IVD 12. External control unit 90 may comprise dedicated hardware and/or software, or may be partially or entirely implemented in standard hardware and/or software, such as a smartphone.

Figure 5:
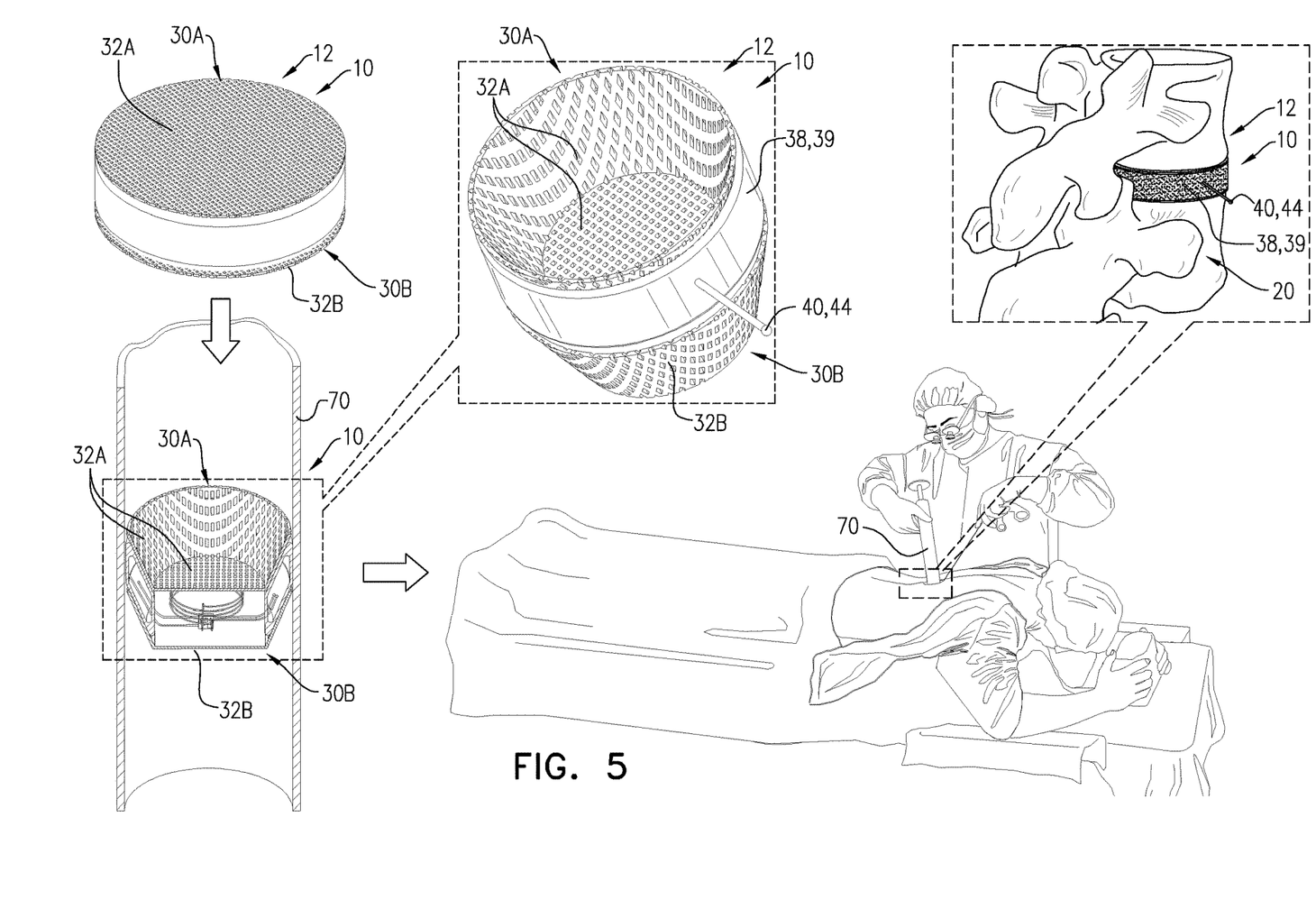
FIG. 5 is a schematic illustration of the implantation of the artificial IVD of FIG. 1, in accordance with an application of the present invention.

Reference is now made to FIG. 5, which is a schematic illustration of the implantation of artificial IVD 12, in accordance with an application of the present invention.

In some applications of the present invention, a method of treating spinal column 20 is provided. A degenerated intervertebral disc is removed from between intervertebral surfaces of spinal column 20. Artificial IVD 12 is implanted such that (a) oppositely-facing outward surfaces 32A and 32B of the two endplates 30A and 30B of artificial IVD 12 engage the intervertebral surfaces of the spinal column, respectively, and (b) one or more extra-chamber exposed electrode surfaces 44 of artificial IVD 12 are located outside chamber 34, in a vicinity of chamber 34 (e.g., within 10 mm, such as within 5 mm, e.g., within 2 mm of lateral wall 38 of chamber 34, such as in physical contact with lateral wall 38 of chamber 34 (e.g., for applications in which band 180 serves as the one or more extra-chamber exposed electrode surfaces 44 of artificial IVD 12, as described hereinbelow with reference to FIG. 6. Control circuitry 50 is activated to drive at least one 42A of the intra-chamber exposed electrode surfaces 42 and at least one of the extra-chamber exposed electrode surfaces 44 to electroosmotically drive liquid from outside chamber 34 to inside chamber 34, and, optionally, to provide any of the additional functions described hereinabove.

Typically, artificial IVD 12 is implanted while chamber 34 is deflated, which allows artificial IVD 12 to assume a collapsed configuration for delivery while removably disposed in a relatively small delivery shaft 70, thereby allowing implantation in a minimally-invasive surgical procedure.

For some applications, when artificial IVD 12 is in the collapsed configuration, outward surface 32A of endplate 30A is concave when viewed from outside artificial IVD 12 and outward surface 32B of endplate 30B is convex when viewed from outside artificial IVD 12.

Activation of control circuitry 50 to electroosmotically drive liquid inside chamber 34 results in inflation of chamber 34 over time. In configurations in which flexible support 60 if provided, the flexible support provides some support to the two endplates 30A and 30B before chamber 34 is filled with liquid.

Optionally, artificial IVD 12 comprises a port (e.g., a self-sealing port), and initial filling of chamber 34 (typically with liquid) is performed by injection through the port.

Alternatively, for some applications, one or more of intra-chamber exposed electrode surfaces 42 are disposed in physical contact with (e.g., line) an inner surface of electroosmotic membrane 39 of lateral wall 38. Even in configurations in which electroosmotic membrane 39 is hydrophobic, the membrane wets after artificial IVD 12 has been in the subject's body for a little while. This wetting is sufficient to start the hydrolysis described hereinabove.

Figure 6:
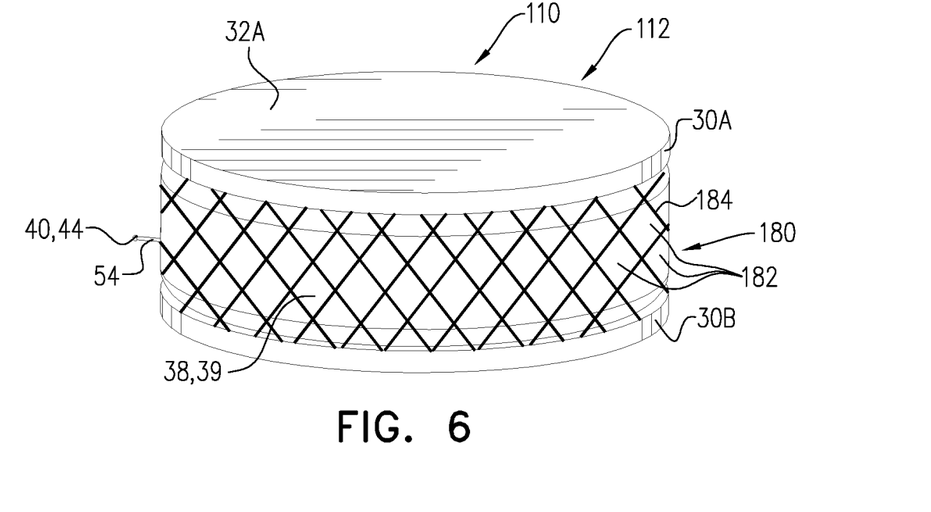
FIG. 6 is a schematic illustration of another artificial IVD system, comprising an artificial IVD, in accordance with an application of the present invention.

Reference is now made to FIG. 6, which is a schematic illustration of an artificial IVD system 110, comprising an artificial IVD 112, in accordance with an application of the present invention. Except as described below, artificial IVD system 110 and artificial IVD 112 are identical to artificial IVD system 10 and artificial IVD 12, respectively, described hereinabove with reference to FIGS. 1-5.

Artificial IVD 112 further comprises a band 180, which is disposed outside and surrounding lateral wall 38 of chamber 34, and which is configured to constrain lateral expansion of chamber 34. For example, band 180 may prevent chamber 34 from over-expanding and perhaps bursting, and/or may enhance downward and/or upward forces on endplates 30A and 30B.

Typically, band 180 is shaped so as to define many openings 182 to allow body fluid to contact electroosmotic membrane 39 of lateral wall 38. For some applications, band 180 comprises a mesh 184, e.g., a stent shaped so as to define a mesh. For example, the mesh (or stent) may comprise a metal, such as Nitinol. Optionally, the mesh is elastic.

For some applications in which band 180 comprises a metal, band 180 serves as the one or more extra-chamber exposed electrode surfaces 44 of artificial IVD 12 (configuration not shown), which case external support structure 54 is not provided.

In some applications of the present invention, the techniques and apparatus described herein are combined with techniques and apparatus described in one or more of the following applications, which are assigned to the assignee of the present application and are incorporated herein by reference:

U.S. Pat. No. 8,577,469 to Gross
U.S. Pat. No. 9,731,122 to Gross
U.S. Pat. No. 9,770,591 to Gross et al.
US Patent Application Publication 2019/0001124 to Gross et al.
U.S. Pat. No. 9,950,156 to Gross et al.
PCT Publication WO 2018/051338 to Gross et al.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
    (a) an artificial intervertebral disc (IVD) for replacement of a degenerated intervertebral disc in a spinal column of a subject, the artificial IVD comprising:
        two endplates having oppositely-facing outward surfaces configured to engage respective intervertebral surfaces of the spinal column;
        a chamber, which is disposed between oppositely-facing inner surfaces of the two endplates, and which comprises a lateral wall comprising an electroosmotic membrane; and
        a plurality of exposed electrode surfaces, including (i) one or more intra-chamber exposed electrode surfaces, which are located within the chamber; and (ii) one or more extra-chamber exposed electrode surfaces, which are located outside the chamber, in a vicinity of the chamber; and
    (b) control circuitry, which is configured to:
        drive at least one of the one or more intra-chamber exposed electrode surfaces and at least one of the one or more extra-chamber exposed electrode surfaces to electroosmotically drive liquid from outside the chamber to inside the chamber, and
        drive at least two of the exposed electrode surfaces to increase a pressure in the chamber by generating a gas in the chamber by electrolysis of water of the liquid in the chamber.

2. The apparatus according to claim 1, wherein the control circuitry is configured to drive the at least one of the one or more intra-chamber exposed electrode surfaces and the at least one of the one or more extra-chamber exposed electrode surfaces to electroosmotically drive the liquid from outside the chamber to inside the chamber by configuring the at least one of the intra-chamber exposed electrode surfaces to be a cathode, and the at least one of the extra-chamber exposed electrode surfaces to be an anode.

3. The apparatus according to claim 1, wherein the artificial IVD further comprises a wire coil, which is configured to receive electromagnetically transmitted energy for electroosmotically driving the liquid from outside the chamber to inside the chamber.

4. The apparatus according to claim 1,
wherein the artificial IVD further comprises a pressure sensor, which is arranged to sense a pressure within the chamber, and
wherein the control circuitry is configured to drive the at least one of the one or more intra-chamber exposed electrode surfaces and the at least one of the one or more extra-chamber exposed electrode surfaces to electroosmotically drive the liquid at least in part based on the sensed pressure.

5. The apparatus according to claim 1, wherein the control circuitry is configured to drive the at least one of the one or more intra-chamber exposed electrode surfaces and the at least one of the one or more extra-chamber exposed electrode surfaces to electroosmotically drive the liquid by applying a voltage of no more than 1.2 V between the at least one of the one or more intra-chamber exposed electrode surfaces and the at least one of the one or more extra-chamber exposed electrode surfaces.

6. The apparatus according to claim 1,
wherein the artificial IVD comprises a plurality of the intra-chamber exposed electrode surfaces, and
wherein the control circuitry is configured to drive at least two of the intra-chamber exposed electrode surfaces to generate the gas in the chamber by electrolysis of water of the liquid in the chamber.

7. The apparatus according to claim 1, wherein the control circuitry is configured to drive at least one of the one or more intra-chamber exposed electrode surfaces and at least one of the one or more extra-chamber exposed electrode surfaces to generate the gas in the chamber by electrolysis of water of the liquid in the chamber.

8. The apparatus according to claim 7, wherein the control circuitry is configured to drive the at least one of the one or more intra-chamber exposed electrode surfaces and the at least one of the one or more extra-chamber exposed electrode surfaces to generate the gas in the chamber by configuring the at least one of the intra-chamber exposed electrode surfaces to be an anode, and the at least one of the extra-chamber exposed electrode surfaces to be a cathode.

9. The apparatus according to claim 1, wherein the control circuitry is configured to:
ascertain a level of motion of the artificial IVD, and
drive the at least two of the exposed electrode surfaces to generate the gas at least in part based on the ascertained level of motion.

10. The apparatus according to claim 9,
wherein the artificial IVD further comprises a motion sensor, which is arranged to sense the level of motion of the artificial IVD, and
wherein the control circuitry is configured to ascertain the level of motion based on the level of motion sensed by the motion sensor.

11. The apparatus according to claim 9,
wherein the artificial IVD further comprises a pressure sensor, which is arranged to sense a pressure within the chamber, and
wherein the control circuitry is configured to ascertain the level of motion based on a rate of change of the sensed pressure within the chamber.

12. The apparatus according to claim 1,
wherein the artificial IVD further comprises a pressure sensor, which is arranged to sense a pressure within the chamber, and
wherein the control circuitry is configured to drive, at least in part based on the sensed pressure, the at least two of the exposed electrode surfaces to generate the gas.

13. The apparatus according to claim 1, wherein the artificial IVD further comprises a flexible support, which is disposed between the two endplates and regulates relative movement of the two endplates.

14. The apparatus according to claim 13, wherein the chamber is annular and surrounds the flexible support.

15. The apparatus according to claim 14, wherein the flexible support is shaped so as to define a compartment.

16. The apparatus according to claim 15, wherein the artificial IVD further comprises a wire coil, which is located within the compartment of the flexible support, and is configured to receive electromagnetically transmitted energy for electroosmotically driving the liquid from outside the chamber to inside the chamber.

17. The apparatus according to claim 15, wherein the artificial IVD further comprises a motion sensor, which is located within the compartment of the flexible support.

18. The apparatus according to claim 1, wherein the control circuitry is configured to:
ascertain a level of motion of the artificial IVD, and
drive the at least one of the one or more intra-chamber exposed electrode surfaces and the at least one of the one or more extra-chamber exposed electrode surfaces to electroosmotically drive the liquid at least in part based on the ascertained level of motion.

19. The apparatus according to claim 18,
wherein the artificial IVD further comprises a pressure sensor, which is arranged to sense a pressure within the chamber, and
wherein the control circuitry is configured to ascertain the level of motion based on a rate of change of the sensed pressure within the chamber.

20. The apparatus according to claim 1, wherein the artificial IVD further comprises a band, which is disposed outside and surrounding the lateral wall of the chamber, and which is configured to constrain lateral expansion of the chamber.

21. The apparatus according to claim 20, wherein the band comprises a metal, and serves as the one or more extra-chamber exposed electrode surfaces.

22. A system comprising the apparatus according to claim 1, wherein the system further comprises a delivery shaft in which the artificial IVD is removably disposed in a collapsed configuration.

23. The system according to claim 22, wherein when the artificial IVD is in the collapsed configuration, the outward surface of one of the two endplates is concave when viewed from outside the artificial IVD and the outward surface of the other of the two endplates is convex when viewed from outside the artificial IVD.

24. A method of treating a spinal column of a subject, the method comprising:

removing a degenerated intervertebral disc from between intervertebral surfaces of the spinal column;

implanting an artificial intervertebral disc (IVD), which includes a plurality of exposed electrode surfaces, including one or more intra-chamber exposed electrode surfaces and one or more extra-chamber exposed electrode surfaces, such that (a) oppositely-facing outward surfaces of two endplates of the artificial IVD engage the intervertebral surfaces of the spinal column, respectively, and (b) the one or more extra-chamber exposed electrode surfaces of the artificial IVD are located outside a chamber of the artificial IVD, in a vicinity of the chamber, wherein the chamber is disposed between oppositely-facing inner surfaces of the two endplates, and includes a lateral wall including an electroosmotic membrane, and wherein the one or more intra-chamber exposed electrode surfaces are located within the chamber; and activating control circuitry to (i) drive at least one of the intra-chamber exposed electrode surfaces and at least one of the extra-chamber exposed electrode surfaces to electroosmotically drive liquid from outside the chamber to inside the chamber, and (ii) drive at least two of the exposed electrode surfaces to increase a pressure in the chamber by generating a gas in the chamber by electrolysis of water of the liquid in the chamber.

25. The method according to claim 24, wherein implanting the artificial IVD comprises implanting the artificial IVD while the chamber is deflated.

26. The method according to claim 25, wherein implanting the artificial IVD while the chamber is deflated comprises implanting the artificial IVD while the outward surface of one of the two endplates is concave when viewed from outside the artificial IVD and the outward surface of the other of the two endplates is convex when viewed from outside the artificial IVD.

27. The method according to claim 25, wherein implanting the artificial IVD while the chamber is deflated comprises implanting the artificial IVD while the artificial IVD is in a collapsed configuration removably disposed in a delivery shaft.

28. The method according to claim 24, wherein the artificial IVD further includes a flexible support, which is disposed between the two endplates and regulates relative movement of the two endplates.

\* \* \* \* \*